(12) United States Patent
Reynier

(10) Patent No.: US 11,997,167 B2
(45) Date of Patent: May 28, 2024

(54) METHOD FOR DATA COMMUNICATION BETWEEN A SERVER SYSTEM AND A FRONT-END COMPUTING DEVICE IN A HEALTHCARE ENVIRONMENT

(71) Applicant: Fresenius Vial SAS, Brézins (FR)

(72) Inventor: Christophe Reynier, Chirens (FR)

(73) Assignee: Fresenius Vial SAS, Brézins (FR)

( * ) Notice: Subject to any disclaimer, the term of this patent is extended or adjusted under 35 U.S.C. 154(b) by 102 days.

(21) Appl. No.: 17/606,643

(22) PCT Filed: Jul. 2, 2020

(86) PCT No.: PCT/EP2020/068695
§ 371 (c)(1),
(2) Date: Oct. 26, 2021

(87) PCT Pub. No.: WO2021/001486
PCT Pub. Date: Jan. 7, 2021

(65) Prior Publication Data
US 2022/0232081 A1 Jul. 21, 2022

(30) Foreign Application Priority Data

Jul. 3, 2019 (EP) .................................... 19305909

(51) Int. Cl.
*H04L 67/141* (2022.01)
*G16H 40/60* (2018.01)
(Continued)

(52) U.S. Cl.
CPC .......... *H04L 67/141* (2013.01); *G16H 40/60* (2018.01); *H04L 67/1097* (2013.01); *H04L 63/08* (2013.01)

(58) Field of Classification Search
CPC ... H04L 67/141; H04L 67/1097; H04L 63/08; H04L 40/60
(Continued)

(56) References Cited

U.S. PATENT DOCUMENTS

| 10,630,814 B2* | 4/2020 | Barnes ................. H04L 67/125 |
| 2009/0048868 A1* | 2/2009 | Portnoy ................. G16Z 99/00 |
| | | 705/2 |

(Continued)

FOREIGN PATENT DOCUMENTS

| CN | 103098086 | 5/2013 |
| CN | 105205766 | 12/2015 |

(Continued)

OTHER PUBLICATIONS

International Search Report and Written Opinion, counterpart International App. No. PCT/EP2020/068695 (dated Sep. 25, 2020) (10 pages).

(Continued)

*Primary Examiner* — Ruolei Zong
(74) *Attorney, Agent, or Firm* — Cook Alex Ltd.

(57) ABSTRACT

In a method for data communication between a server system (3) and a front-end computing device (2) in a healthcare environment the front-end computing device (2) transmits a request for a data connection to a primary interface (30) of the server system (3). The server system (3) processes the request, and a data connection between the server system (3) and the front-end computing device (2) is established as a result of the processing. Herein, said processing includes creating a secondary interface (32) on the server system (3) dedicated to the request and transmitting information to access said secondary interface (32) to the front-end computing device (2), wherein said establishing includes connecting, by the front-end-computing device (2), (Continued)

to said secondary interface (32) using information received from the server system (3).

19 Claims, 8 Drawing Sheets

(51) Int. Cl.
  *H04L 67/1097* (2022.01)
  *H04L 9/40* (2022.01)
(58) Field of Classification Search
  USPC .......................................................... 709/223
  See application file for complete search history.

(56) References Cited

U.S. PATENT DOCUMENTS

| | | | |
|---|---|---|---|
| 2010/0169120 A1* | 7/2010 | Herbst | G16H 40/67 |
| | | | 707/E17.014 |
| 2011/0072379 A1* | 3/2011 | Gannon | G16Z 99/00 |
| | | | 715/781 |
| 2011/0078608 A1* | 3/2011 | Gannon | G16H 10/60 |
| | | | 715/771 |
| 2012/0296673 A1* | 11/2012 | Ackerson | G16H 10/60 |
| | | | 705/3 |
| 2013/0124852 A1 | 5/2013 | Kain et al. | |
| 2013/0138455 A1 | 5/2013 | Saharan | |
| 2015/0234639 A1* | 8/2015 | Allsbrook | G06F 8/20 |
| | | | 717/104 |
| 2018/0139111 A1* | 5/2018 | Lugiai | H04L 67/141 |
| 2018/0214091 A1* | 8/2018 | Baker | A61G 7/018 |
| 2019/0068760 A1* | 2/2019 | Barnes | G16H 40/63 |
| 2020/0023127 A1* | 1/2020 | Simpson | A61M 1/1613 |

FOREIGN PATENT DOCUMENTS

| | | |
|---|---|---|
| EP | 2512097 | 10/2012 |
| WO | WO2014/131729 | 9/2014 |
| WO | WO2019/063249 | 4/2019 |

OTHER PUBLICATIONS

Office Action and Search Report (with English-language translation), counterpart Chinese App. No. 202080045522.7 (dated Aug. 8, 2023) (16 pages).

\* cited by examiner

METHOD FOR DATA COMMUNICATION BETWEEN A SERVER SYSTEM AND A FRONT-END COMPUTING DEVICE IN A HEALTHCARE ENVIRONMENT The present application is a U.S. National Stage of PCT International Patent Application No. PCT/EP2020/068695, filed Jul. 2, 2020, which claims priority to EP Application No. 19305909.4, filed Jul. 3, 2019, both of which are hereby incorporated herein by reference.

The invention relates to a method for data communication between a server system and a front-end computing device in a healthcare environment according to the preamble of claim 1 and to a system for data communication in a healthcare environment.

Within a method of this kind a front-end computing device transmits a request for a data connection to a primary interface of a server system. The server system processes the request, and as a result of the processing a data connection between the server system and the front-end computing device is established.

In a healthcare environment, such as a hospital, typically medical devices (such as infusion stations, for example in the shape of pump devices organized in stacks on racks or standalone pump devices) are connected to a communication network and via the communication network to a hospital information system. Users may access the communication network via front-end computing devices, such as stationary personal computers (PCs), laptop computers, tablet computers or mobile devices such as mobile phones, in order to receive data relating to medical devices or transmit data towards medical devices, for example to monitor ongoing infusion operations or to configure pump devices for example to set up infusion operations.

In a hospital environment, typically a server system in the shape of a back-end server is used to host components which provide services to front-end applications being installed on front-end computing devices. Within such services, typically data is exchanged in an upstream direction from the server system towards a front-end computing device, for example to display data on the front-end computing device to a user via a user interface, or in a downstream direction from the front-end computing device towards the server system for processing data, storing data and transferring data to other devices, such as medical devices in the shape of infusion stations or other servers.

There is a desire to be able to control a data exchange within such a system to allow front-end computing devices to access data relating to medical devices, in particular to receive data in the upstream direction for example to monitor infusion operations or to transmit data in the downstream direction towards a medical device for example for programming the medical device.

WO 2014/131729 A2 describes a system for providing drug library data to a medical device located within a healthcare environment, the system comprising a local network and at least one medical device for administering a drug to a patient, the at least one medical device being located in the healthcare environment and connected to the local network. Drug library data herein is transferred to the at least one medical device via a public communication network.

It is an object of the instant invention to provide a method for data communication between a server system and a front-end computing device in a healthcare environment as well as a system for data communication which allow in an easy way to provide for a data exchange between a front-end computing device and a server system upon a request for a data connection.

This object is achieved by means of a method comprising the features of claim 1.

Accordingly, said processing includes creating a secondary interface on the server system dedicated to the request and transmitting information to access said secondary interface to the front-end computing device, wherein said establishing includes connecting, by the front-end computing device, to said secondary interface using information received from the server system.

A front-end computing device, in particular an application running on a front-end computing device, may wish to access a server system, such as a back-end server in a healthcare environment, for example a hospital. For this, the front-end computing device transmits a request to the server system, which at first is directed to a non-dedicated, primary interface via which different front-end computing devices running different applications may connect to the server system. Upon receiving such request, the server system processes the request, and in the context of the processing creates a secondary interface on the server system dedicated to the request. The server system then transmits information to the front-end computing device which enables the front-end computing device to access said secondary interface to establish a (logical) data connection.

Hence, a first connection to the server system by means of the front-end computing devices takes place via the primary interface, to which the front-end computing device directs its initial request. Upon this request, the server system creates a dedicated, secondary interface, which is dedicated solely to the front-end computing device and the particular request issued by the front-end computing device. After having received information identifying the secondary interface to the front-end computing device, the front-end computing device connects to the secondary interface and in this way establishes a data connection to the server system. Via the data connection, then, data may be exchanged between the front-end computing device and the server system, such connection for example allowing to receive data from the server system for example in order to obtain information of one or multiple infusion stations (e.g., relating to infusion operations carried out on those infusion stations), and—potentially—to transfer data towards the server system in order to for example transmit data to infusion stations, for example for a programming of infusion stations or for a modification of a configuration of an infusion station.

The data connection may be a one-way connection or a two-way connection. In one embodiment, the data connection is one way in that the front-end computing device may receive data via the secondary interface, but may not transmit data to the secondary interface. In this case a data transmission from the front-end computing device towards the server system may take place via the primary interface. The secondary interface hence is a read-only interface. In another embodiment, the data connection may be a two-way connection such that the front-end computing device may receive data from and may transmit data to the secondary interface.

The data connection is established as a logical network connection, defined by e.g. the ports and/or IP addresses of a specific application of the front-end computing device and the secondary interface created on the server system.

The primary interface, also denoted as primary API (API stands for Application Programming Interface) serves to receive all requests from external front-end computing devices, in particular applications run on front-end computing devices. The primary interface may delegate the request to an administration engine of the server system, which processes the request and creates the secondary interface, also denoted as data API.

As a dedicated interface for each request is created, a data transfer can be established in a logical, systematic manner. Herein, one front-end computing device may access the server system via several secondary interfaces, one secondary interface being associated which each request that has been issued from the front-end computing device, in particular one or multiple applications run on the front-end computing device.

The secondary interface herein allows a data transfer, in one embodiment, as specified and allowed for the request. Hence, via the secondary interface only such data may be exchanged which is defined in and by the request and allowed for the request.

For example, within a request it may be defined that a data communication with a specific infusion station shall be enabled. A data connection created via a dedicated secondary interface in that case allows for a data transfer between the requesting entity, in particular a specific application run on the front-end computing device, and the specific infusion station, but does not allow an access of data relating to other infusion stations.

In one embodiment, the processing that is being done in the server system includes a verification by means of an authentication and/or an authorization based on the request according to information included in the request. Hence, based on the request, an authentication and/or an authorization is performed in order to check whether a requesting entity, in particular an application of a front-end computing device, is registered with the server system (authentication) and is allowed to access data which is defined in the request (authorization).

Within the authentication, information relating to the identity of the requesting entity is checked. In one embodiment, authentication may employ a pre-shared key (PSK authentication). Such pre-shared key is known both by the requesting entity, in particular a specific application run on a front-end computing device, and the server system. For the authentication, in the request for example information identifying the requesting entity encoded by the pre-shared key may be provided, wherein the server system is able to decode the information and authenticate the request based on a correct decoding.

In one embodiment, only in case the authentication is successful, the secondary interface is created. If the authentication is not successful, the request is declined, without creating a secondary interface.

In one embodiment, the server system may store information about an authorization of a specific application of a front-end computing device to access data by means of the server system. Herein, for each registered application and each registered front-end computing device a specific set of authorizations may be defined, that is a specific set of data which a particular application and a particular front-end computing device is allowed to access. Within the process of authorization, it is checked whether the requesting entity, in particular a specific application of a front-end computing device, is allowed to access the data that is stated in the request, and only upon successful authorization the requesting entity is allowed access to the data.

For allowing the requesting front-end computing device, in particular a specific application run on the front-end computing device, to establish the data connection to the server system via the secondary interface, relevant information for accessing the secondary interface is transmitted to the front-end computing device by means of the server system. Such information may include, in one embodiment, address information identifying the secondary interface on the network, such as a port number or an IP address of the secondary interface. In addition, credentials may be transmitted to the requesting entity such as a dedicated passphrase or the like, such credentials enabling the requesting entity to access the secondary interface in order to establish the data connection.

Once the front-end computing device has received the information about the secondary interface, the front-end computing device can connect to the secondary interface and hence can establish a data connection. Via the data connection then a data communication between the front-end computing device and the server system can be carried out such that data can be transmitted to the server system for example relating to an infusion station, and/or data can be received from the server system.

The data connection established via the secondary interface may be persistent in that it allows for a steady data communication for example to monitor an ongoing infusion operation over a substantial time span. The data connection may be canceled by the front-end computing device, or may automatically cancel after a predefined time for which the front-end computing device is allowed access, for example in the meaning of a predefined session having a predefined length.

In one embodiment, the server system comprises a data engine for transmitting data to or receiving data from the front-end computing device. The data engine may store information relating to infusion stations or other external service. Via the data engine, data may be transferred to a front-end computing device as defined for a specific secondary interface, or data may be transferred to the server system by means of the front-end computing device.

The data engine herein may, in the upstream direction, provide data to the secondary interface for transmission to the front-end computing device. In the downstream direction, in turn, the data engine may receive data, in one embodiment, from the front-end computing device via the primary interface. Hence, only in the upstream direction data transmission takes place via the secondary interface.

In one embodiment, the data engine may communicate with at least one infusion station using a driver module configured to receive, in an upstream direction, data from and/or transmit, in a downstream direction, data to at least one infusion station.

In particular, the driver module serves to provide for a communication with one or multiple infusion stations, wherein the infusion stations may comprise one or multiple different pump devices of different types employing different protocols for communicating data. A driver module in particular manages a connection to an infusion station, is enabled to communicate using a communication protocol required by a specific infusion station, and hence is enabled to process data received from an infusion station and for transmission towards said infusion station using a particular communication protocol associated with that infusion station.

In a further embodiment, the data engine may communicate with the front-end computing device using a virtual device module configured to transmit, in the upstream direction, data to and receive, in the downstream direction, data from the front-end computing device, wherein the driver module, in the upstream direction, processes data received from the at least one infusion station using said first communication protocol to provide said data to the virtual device module and/or, in the downstream direction, processes data received from the virtual device module to transmit said data to the at least one infusion station using said first communication protocol. Herein, the virtual device module includes a data model defining a plurality of data structures in which data relating to the at least one infusion station is stored A virtual device module, hence, provides for a communication—via a created, dedicated secondary interface—of data with a front-end computing device. The virtual device module comprises a data model defining a plurality of data structures. Within the data model, data processed by the driver module is stored in defined, dedicated data structures, such that data received from one or multiple infusion devices is organized in a defined structure according to the data structures of the data model. Within the virtual device module data relating to one or multiple infusion devices hence is organized in a structure independent from communication protocols by means of which data is communicated in between one or multiple infusion devices and the driver module.

The organization of data relating to one or multiple infusion devices within the data model included in the virtual device module allows to communicate with one or multiple front-end computing devices using a common communication protocols. In particular, data can be communicated from the virtual device modules towards one or multiple front-end computing devices using a common communication protocol, which is independent from any communication protocol via which data is communicated between the infusion devices and the virtual device module.

Hence, the data communication in between front-end computing devices and the virtual device module is independent from any data communication in between infusion devices and the virtual device module (via one or multiple driver modules). By means of the virtual device module a generic data model is provided which allows for a data transfer in between the front-end computing devices and the virtual device module. Data may be exchanged in between the virtual device module and front-end computing devices using a common communication protocol, the data communication being independent from a data communication in between the driver module and a related infusion device (involving a specific communication protocol used for the data communication).

In one embodiment, different driver modules may communicate with different infusion stations using different first communication protocols. In particular, infusion stations of different kinds may exist, comprising for example pump devices of different types (e.g. volumetric infusion pumps or syringe infusion pumps) and belonging to different device families (e.g., Fresenius currently is offering pump devices in the so-called Agilia family and other pump devices for example for an enteral feeding in the so-called Amika family). In addition, one infusion station, being constituted of for example a standalone pump device or a stack of pumps combined for example on a rack, may communicate using different communication channels, such as a wireless communication channel using Wi-Fi or a wire-bound communication channel using for example an Ethernet connection.

Herein, for each protocol that is being used by any infusion station, one driver may exist and may be installed for example on a server system, such that the driver module enables the communication between an infusion station making use of that protocol and a corresponding virtual device module, such that data may be exchanged between the infusion station and the virtual device module.

Hence, a first driver module may for example exist for a communication with an infusion station making use of a first communication channel, such as a wire-bound communication channel such as an Ethernet connection. Such driver module may enable for example a communication making use of an Ethernet protocol. A second driver module may exist for a communication with an infusion station making use of a second communication channel, such as a wireless communication channel, enabling a communication making use of a Wi-Fi (wireless LAN) protocol, a Bluetooth protocol, an NFC (Near Field Communication) protocol or the like. A third driver module may exist for an infusion station of a different type and for example belonging to a different device family. Overall, one driver module may be provided for each communication channel between an infusion station and the server system.

In one embodiment, the first communication protocol may be based on WiFi, HTTP, or Ethernet. Such protocol may be standardized. The WiFi protocol for example is standardized in the IEEE 802.11 standard. The Ethernet protocol is standardized in the IEEE 802.3 standard. In addition, based on standardized protocols, proprietary modifications implemented by a pump manufacturer may be employed, such that a protocol used by a particular infusion station may, in addition to the standardized protocol schematic, employ a proprietary scheme.

A second communication protocol used for communicating in between the virtual device module and a front-end computing device may be different than the first communication protocol, or may be the same. For example, the second communication protocol may be based on AMQP or HTTP. Herein, a common communication protocol may be used for communication in between front-end computing devices and one or multiple virtual device modules, the common, second communication protocol being independent from any communication protocol that is being used for communication in between infusion devices and associated driver modules.

Whereas different driver modules exist for different infusion stations and use different communication protocols for communicating with different infusion stations, the communication between the virtual device module and different front-end computing devices via different dedicated secondary interfaces takes place using a common protocol scheme, such that all front-end computing devices communicate with a virtual device module making use of the same communication protocol or a set of communication protocols.

In one embodiment, the virtual device module, as the second communication protocol, uses an upstream protocol in the upstream direction and a downstream protocol different than the upstream protocol in the downstream direction. Hence, different protocols are employed dependent on whether a communication takes place in the upstream direction or in the downstream direction.

Whereas the upstream protocol may be based for example on AMQP, the downstream protocol may for example be based on HTTP.

The use of different protocols in the upstream direction and in the downstream direction is based on that the virtual device module shall, in one embodiment, buffer data received from one or multiple infusion stations or from one or multiple front-end communication devices in the data model making use of the data structures being defined by the data model. In particular, a virtual device module may store data relating to an identity of a pump device of an infusion station, a status of a pump device of an infusion station, and capabilities of a pump device of an infusion station in associated, predefined data structures. Hence, the virtual device module consolidates data relating to pump devices and stores the data in an organized fashion in a structured, generic data model, such that a front-end computing device may receive data from the virtual device module via a dedicated secondary interface in order to obtain information relating to a particular pump device or a particular infusion station comprising multiple pump devices.

The structure of the data model is herein, in one embodiment, independent from the virtual device module, different virtual device modules using the same generic data model having the same structure.

In the data model, data may be stored for example using XML (Extended Markup Language).

For communicating data in between a driver module and an associated virtual device module a protocol allowing for a buffering of data may be employed, in particular AMQP (AMQP stands for Advanced Message Queuing Protocol), AMQP being an open standard application layer protocol for message oriented middleware and allowing for a queuing of data messages.

In particular, the virtual device module may store information relating to an identity of a pump device, such as the pump device's family, the type of the pump device and a version of a hardware or a software currently installed on the pump device.

In addition or alternatively, the virtual device module may store information relating to the pump status such as the connectivity of the pump device, an infusion status of an ongoing infusion operation, a location of a pump device on a rack, and a location of the pump device in a healthcare environment such as a hospital. Information relating to the infusion status may include a drug of an infusion operation, a dosage, a dose rate, a time of infusion, a time remaining of an infusion, patient information and the like.

In addition or alternatively, the virtual device module may store information relating to capabilities of a pump device, wherein the capabilities may depend on a communication channel by means of which the pump device is connected to a communication network and hence is enabled to communicate with a corresponding driver module. In particular, the capabilities may include clinical functions which are available depending on a communication channel by which the pump device is connected. For example, if a pump device is connected by means of a wireless communication channel, only a subset of clinical functions may be available in comparison to other communication channels, such as wire-bound communication channels. Such clinical functions may for example relate to an auto-programming, an auto-documentation, a drug library configuration, a technical configuration, a firmware upload, and a device event log relating to a pump device. For example, a firmware upload may be available only for a wire-bound communication channel, but not if the pump device is connected via a wireless communication channel.

For predefined kinds of information herein predefined data structures may exist in the data model included in the virtual device module, such that information relating to an infusion device is stored in predefined data structures, independent from any communication protocol that is being used for communicating data in between the infusion devices and the associated driver modules.

In one embodiment, each driver module is implemented as a dynamic-link library (in short: dll) or a windows service. A dynamic-link library represents a shared library which may be employed by software applications. Such dynamic-link libraries allow in a modular fashion to provide executable programming code which may be commonly executed by different applications. Dynamic-link libraries having the file ending .dll are in particular employed in a window operating system environment.

In one embodiment, the virtual device module groups infusion devices of infusion stations belonging to a common device family. Herein, for each device family one virtual device module may be installed, such that one virtual device module per family exists. Within a virtual device module information relating to pump devices belonging to the same family, but potentially being of different type (for example volumetric infusion pumps and syringe infusion pumps) may be stored and accessed by front-end computing devices.

For a data communication in between a driver module and a corresponding virtual device module a common protocol such as AMQP may be employed, wherein each driver module communicates with a corresponding virtual device module making use of the same protocol. One virtual device module herein may communicate with different driver modules, namely one driver module for each protocol that a pump device of a device family is using.

The object is also achieved by means of a system for data communication in a healthcare environment comprising: a server system comprising a primary interface, and a front-end computing device configured to transmit a request for a data connection to the primary interface of the server system, wherein the server system is configured to process said request in order to enable a data connection between the server system and the front-end computing device to be established as a result of the processing. Herein, the server system is configured, during the processing, to create a secondary interface on the server system dedicated to the request and to transmit information to access said secondary interface to the front-end computing device, wherein the front-end-computing device is configured to connect to said secondary interface using information received from the server system.

The advantages and advantageous embodiments described above for the method equally apply also to the system, such that it in this respect shall be referred to the above.

The idea underlying the invention shall subsequently be described in more details with reference to the embodiments shown in the figures. Herein:

Figure 3:
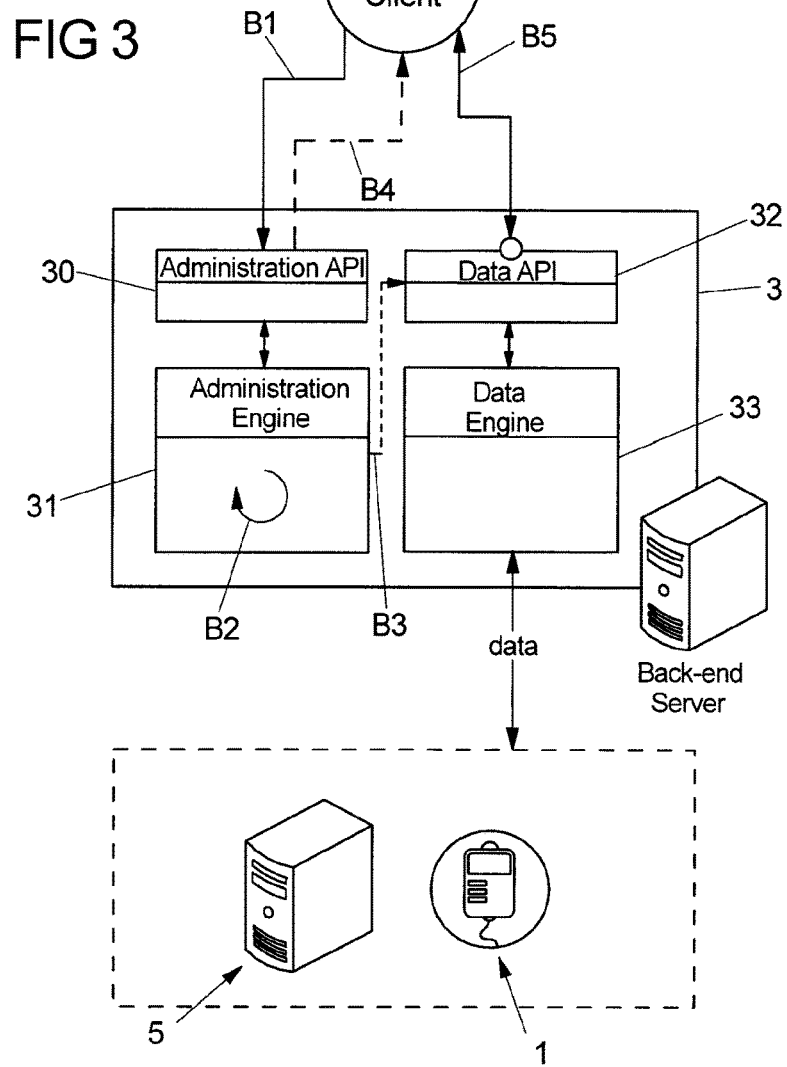
Figure 4:
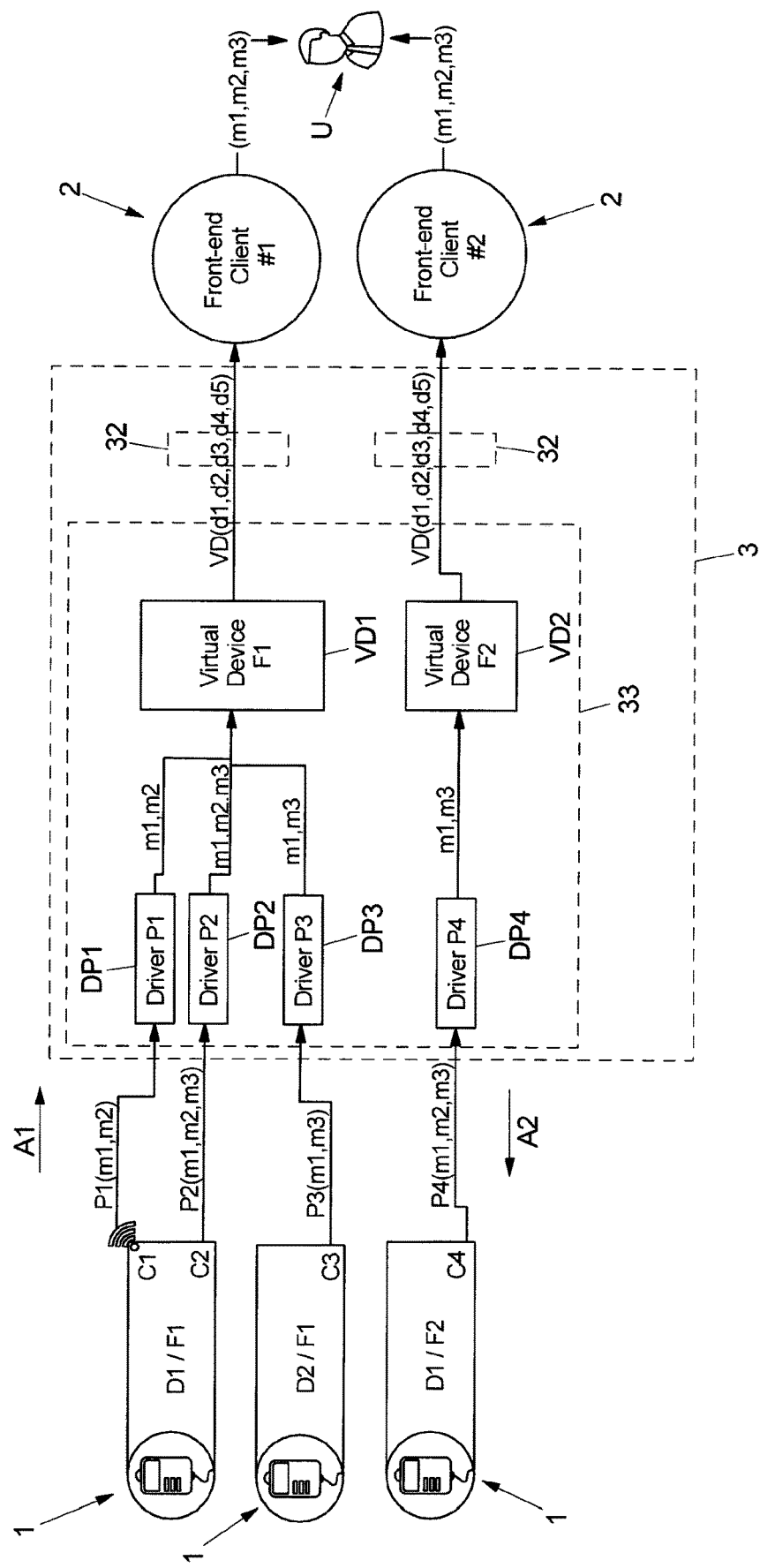
Figure 5:
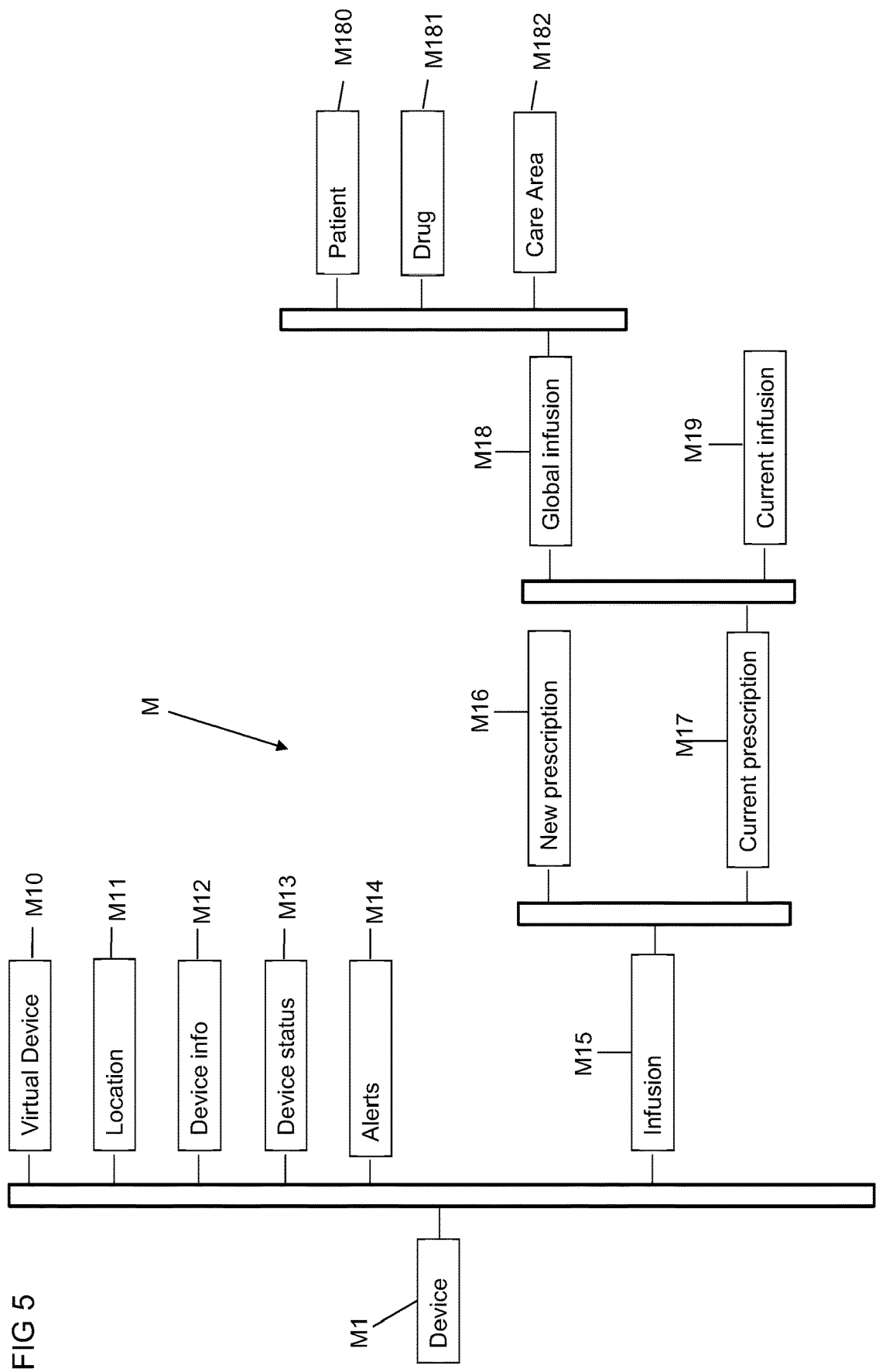
Figure 6:
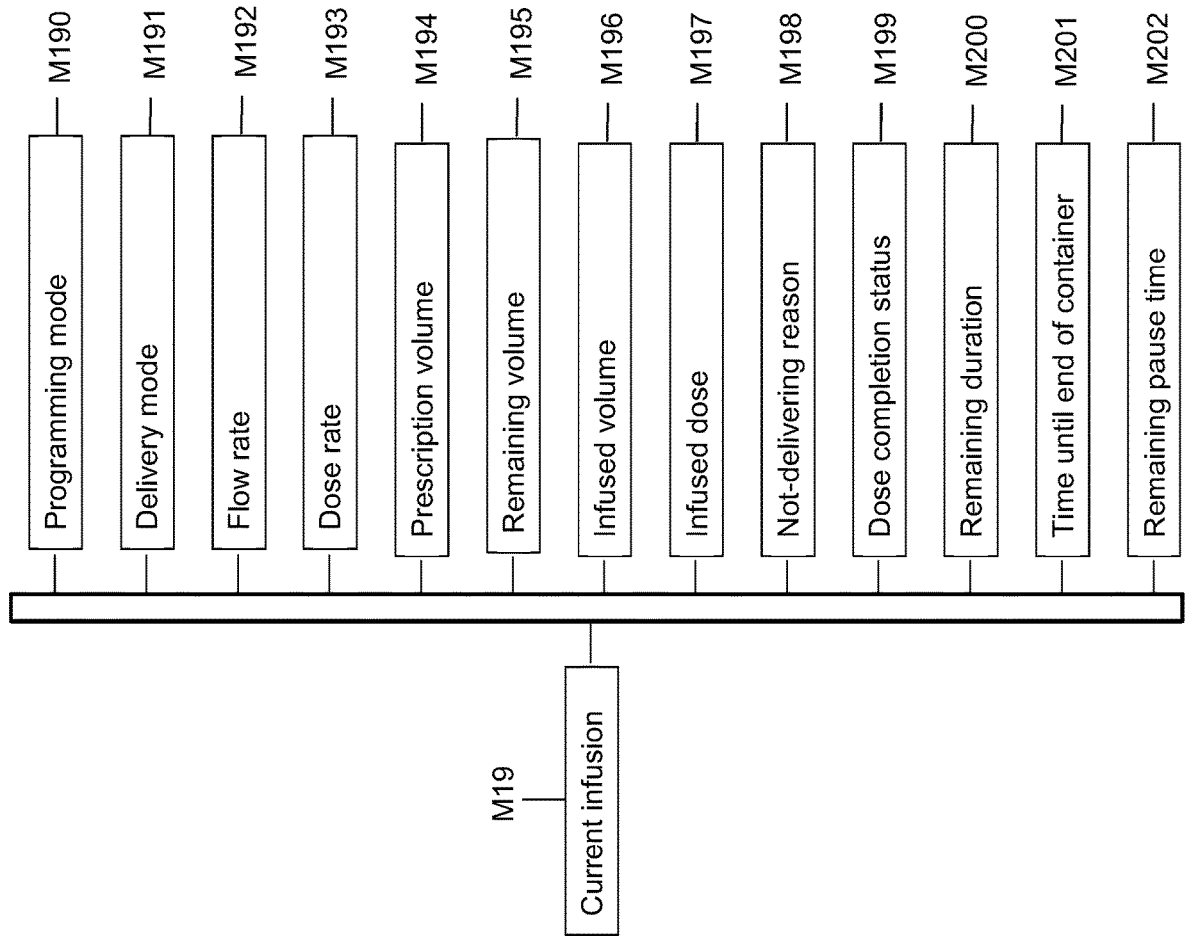
Figure 7:
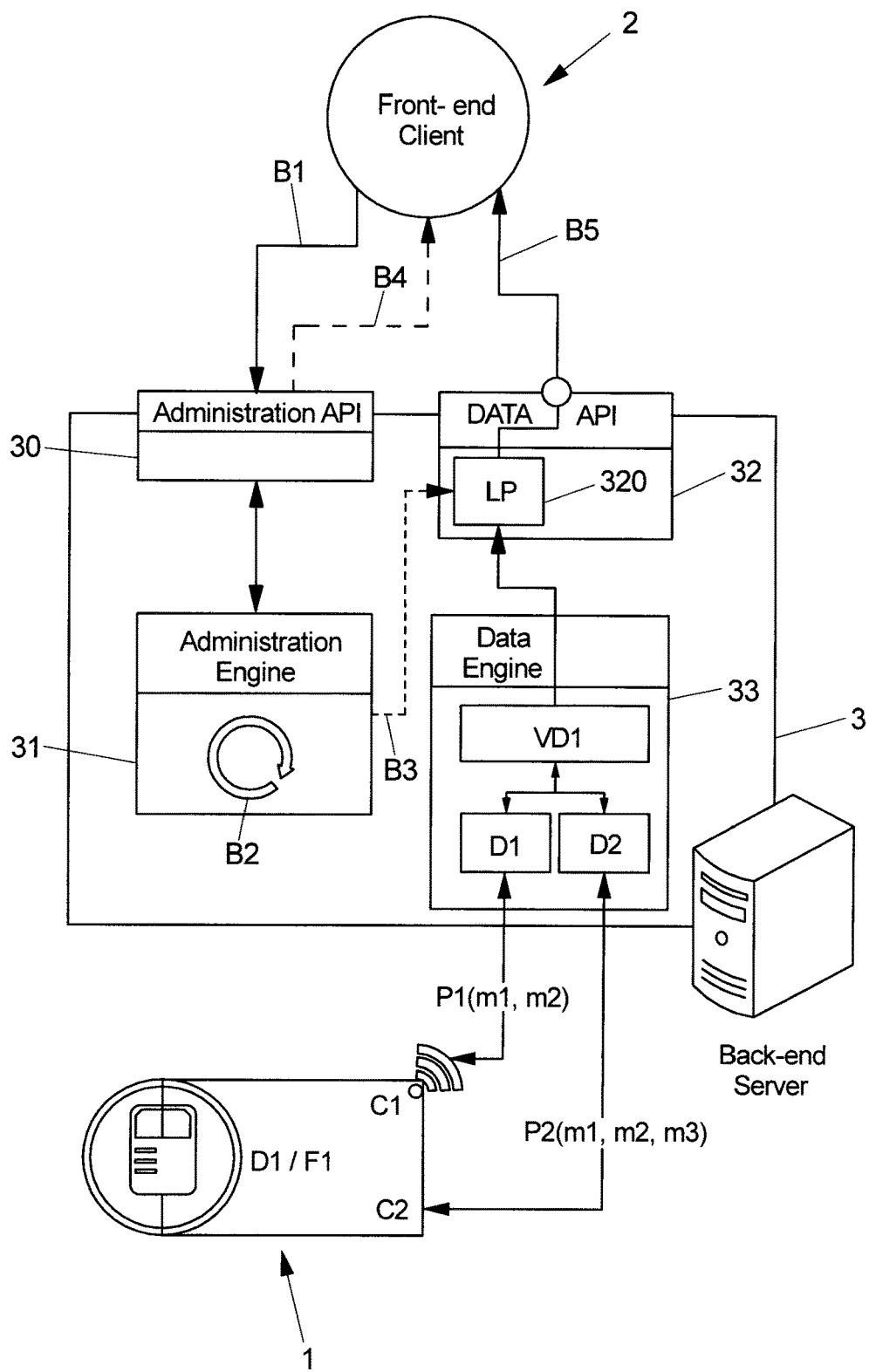
Figure 8:
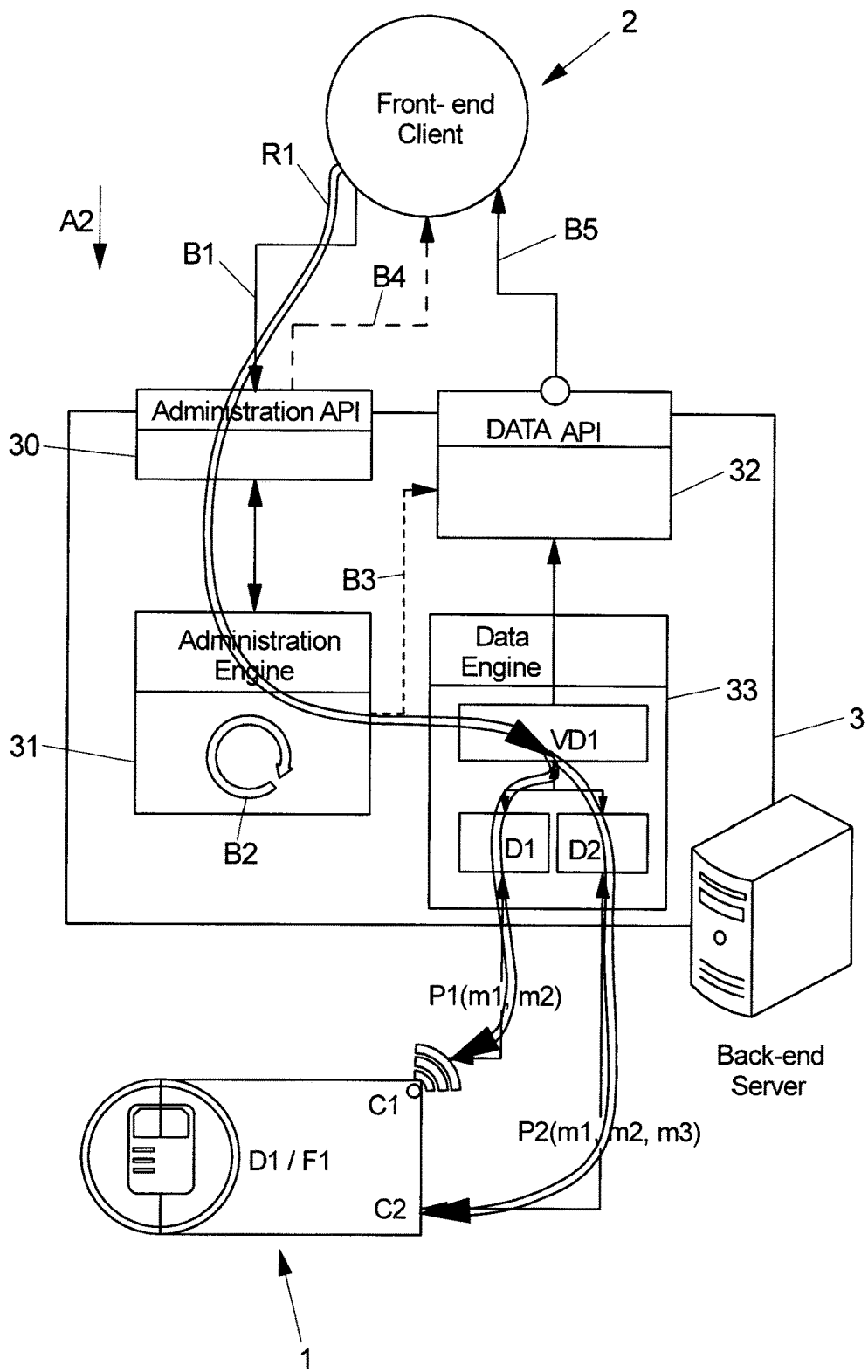

FIG. 3 shows a schematic drawing of a setup of a server system for establishing a data connection in between a front-end computing device and the server system; and FIG. 4 shows a communication in between infusion stations and front-end computing devices employing an intermediate layer comprised of driver modules and virtual device modules for translating and abstracting a communication of data in between the infusion stations and the front-end computing devices;

FIG. 5 shows a schematic view of a data model including data structures for storing data in an organized fashion in a virtual device module;

FIG. 6 shows a schematic view of a data structure including sub-structures;

FIG. 7 shows a schematic drawing of a setup of a server system for establishing a data connection in between a front-end computing device and the server system, employing a data engine comprising driver modules and virtual device modules for translating and abstracting a communication of data in between infusion stations and front-end computing devices;

FIG. 8 shows a schematic drawing of a downstream data communication; and

Figure 9:
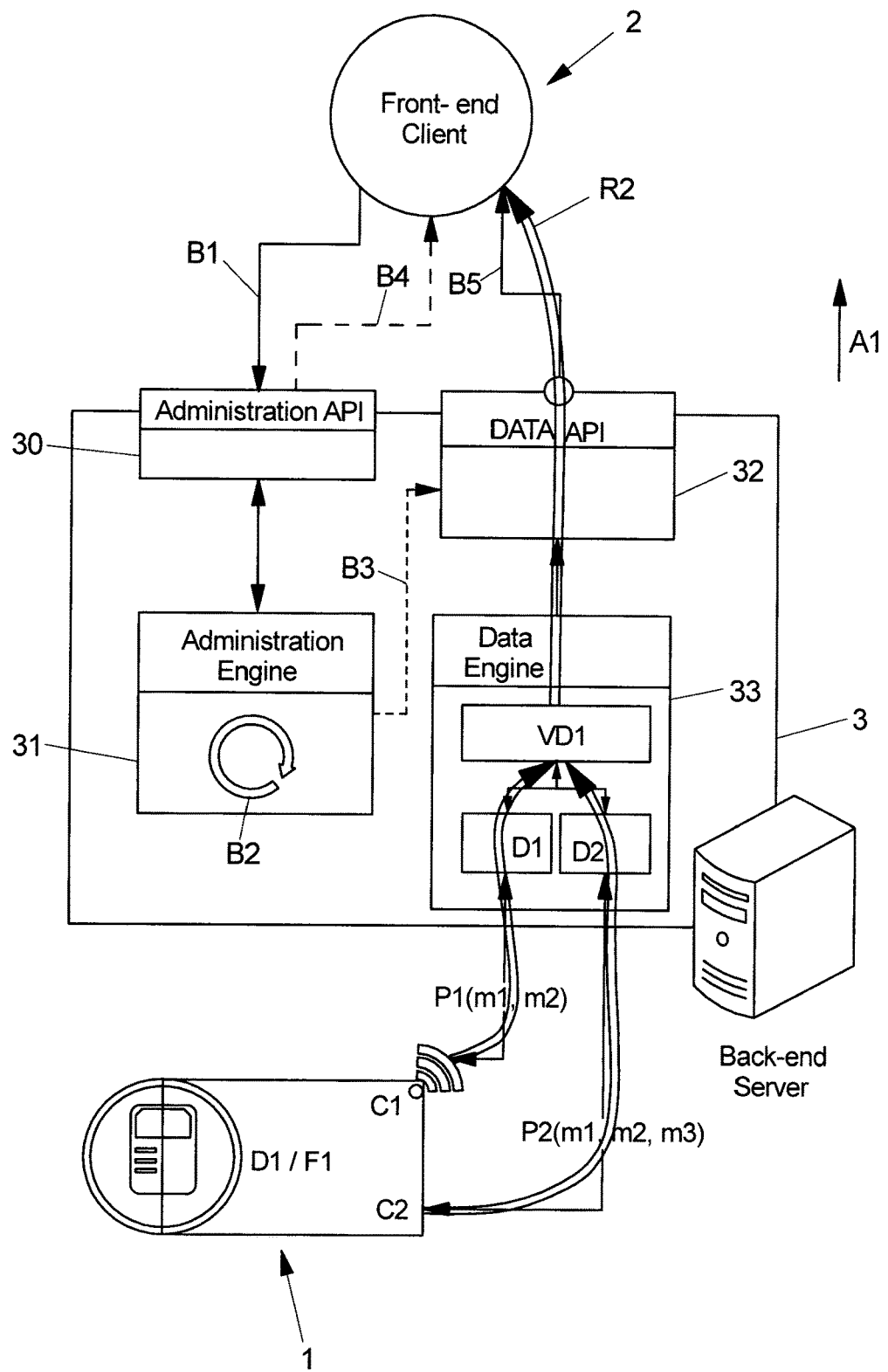

FIG. 9 shows a schematic drawing of an upstream data communication.

Figure 1:
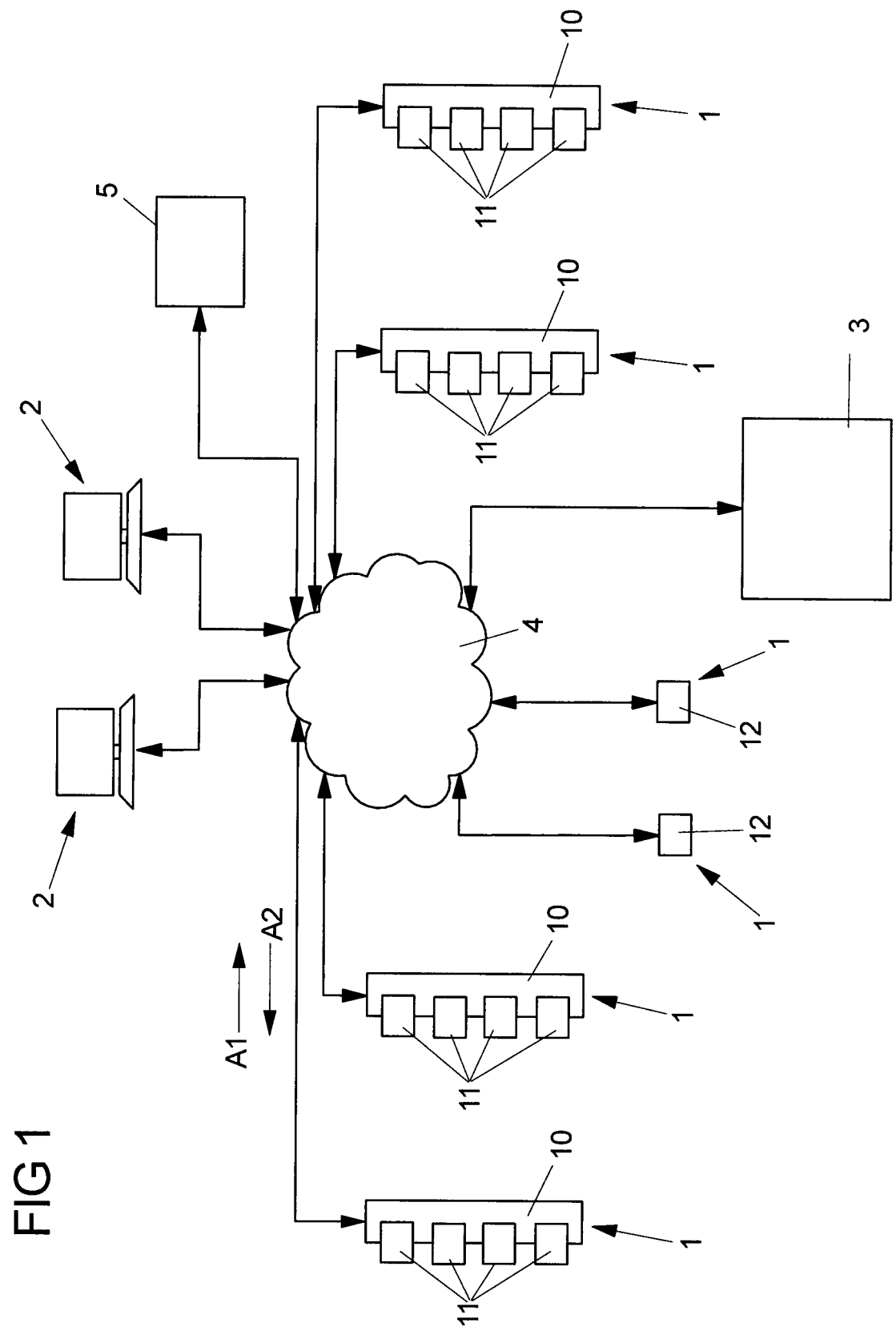
FIG. 1 shows a schematic drawing of a system for data communication in a healthcare environment.

FIG. 1 shows, in a schematic drawing, a setup as it may be found in a healthcare environment, such as a hospital.

Namely, within a healthcare environment, infusion stations 1 such as stacks of pump devices 11 placed in an organized fashion on racks 10 or standalone pump devices 12 may be connected to a hospital communication network 4 and via the communication network 4 to a hospital information system (HIS). In addition, front-end computing devices 2 such as stationary personal computers (PC), laptop computers, tablet computers or mobile communication devices such as mobile phones are connected to the communication network 4. A server system 3, in particular a back-end server comprised of one or multiple (distributed) physical server entities, is connected to the communication network 4, the communication network 4 enabling a data communication between the infusion stations 1, the front-end computing devices 2 and the server system 3. Additional servers 5 may be connected to the communication network 4, such servers 5 storing for example data, or serving specific clinical functions, for example in the context of distributing drug library data to medical devices throughout a healthcare environment.

In the context of a healthcare environment, users may wish to set up infusion operations to be carried out by one or multiple pump devices 11, 12, such pump devices 11, 12 being arranged throughout the healthcare environment in different wards and different rooms at the bedside of different patients. For this, a user may wish to transfer programming data to one or multiple pump devices 11, 12 in order to set up an infusion operation, or to manage and administer the configuration of one or multiple pump devices 11, 12, for example by transferring drug library data to one or multiple pump devices 11, 12, such drug library data providing general boundaries and guidelines for setting up infusion operations, such as boundaries for a dose rate for particular drugs and the like.

In addition, a user may wish to monitor an ongoing infusion operation carried out by one or multiple pump devices 11, 12, requiring a data transfer from pump devices 11, 12 towards front-end computing devices 2 via which a user can access the data.

Figure 2:
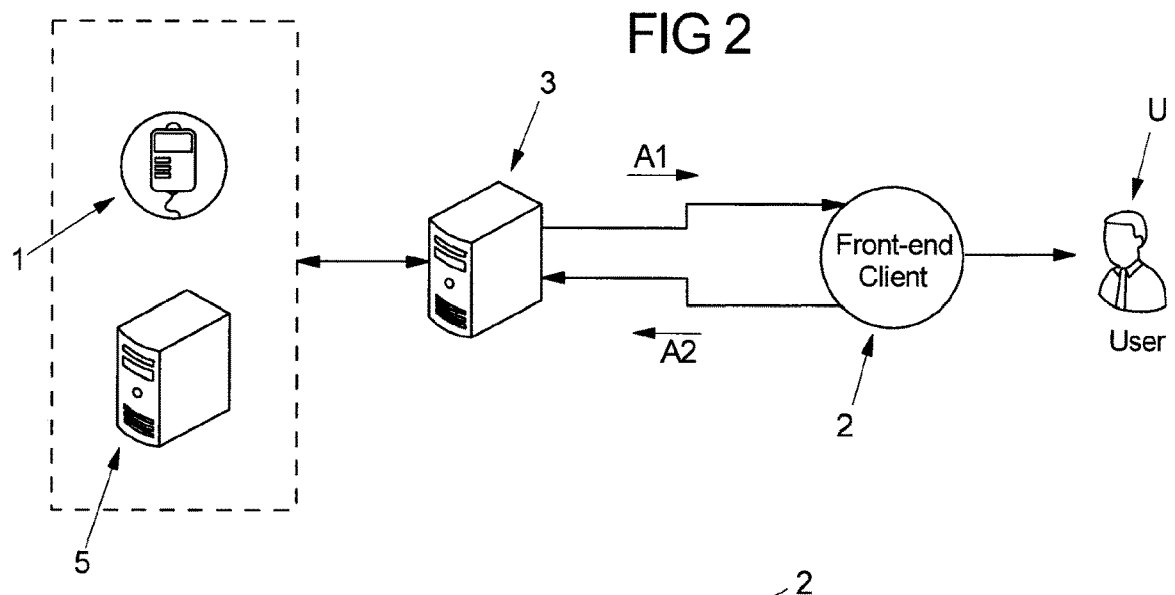
FIG. 2 shows a schematic drawing of a connection of a front-end computing device to a server system.

Referring now to FIG. 2, in a healthcare environment a communication of data may take place via a server system 3, in particular a so-called back-end server providing for a data communication between front-end computing devices 2 and medical devices such as infusion stations 1 and other servers 5 hosting data or applications for specific services. A front-end computing device 2 herein may communicate with the server system 3 in an upstream direction A1 (from the server system 3 towards the front-end computing device 2) and in a downstream direction A2 (from the front-end computing device 2 towards the server system 3). A front-end computing device 2, such as a stationary PC, a laptop computer, a tablet computer or a mobile device such as a mobile phone may provide data to a user U, for example via a user interface such as a display.

Referring now to FIG. 3, for accessing the server system 3 a front-end computing device 2 may issue a request and may send the request to a primary interface 30 of the server system 3, defined for example by a port number and an IP address or the like and providing for a generic data interface for different front-end computing devices 2 to connect to the server system 3 (action B1 in FIG. 3). By means of the request a specific application of the front-end computing device 2 may request access to a specific set of data, for example data relating to a specific infusion station 1, to a specific family of infusion stations 1, to a set of medical devices located in a specific location, to a specific set of data hosted on a server 5, such as a drug library server, or the like.

Upon receiving the request, the request within the server system 3 is forwarded to an administration engine 31, which processes the request (action B2 in FIG. 3). Within the processing, the request may for example be verified by carrying out an authentication and an authorization.

Within the request, for example data relating to an identification of the requesting entity, in particular a specific application running on a specific front-end computing device 2, may be provided, for example an ID encoded by a pre-shared key (PSK) which is also known to the server system 3, in particular the administration engine 31. For carrying out an authentication, such data may be processed by means of the pre-shared key also known to the administration engine 31, and by means of the processing the request is authenticated, i.e., it is verified that the request indeed comes from a specifically identified entity, and the entity is allowed to request an access to the server system 3.

In the administration engine 31, in addition, data defining a specific authorization for a specific requesting entity, such as a specific application of a specific front-end computing device 2, may be stored, such authorization information defining what data a specific entity may be allowed to access. Within the authorization procedure it is in particular checked whether the requesting entity is authorized to access the data that it requests access to.

If the authentication and the authorization are successful, a secondary interface 32 is created (action B3 in FIG. 3). The secondary interface 32 is dedicated to the specific request and shall provide a data communication only for that specific request. The secondary interface 32 is identified by relevant network address information, such as a port number and/or an IP address. In addition, credentials may be defined for the secondary interface 32, an entity being allowed access to the secondary interface 32 only if correct credentials are provided when setting up the connection.

Once the secondary interface 32 is created, information relating to the secondary interface 32 are forwarded to the front-end computing device 2 (action B4), in particular the requesting entity, namely the specific application run on the front-end computing device 2. The information in particular includes address information such as the port number and/or the IP address, and also credentials allowing to access the secondary interface 32.

Once the information is received, the front-end computing device 2 can connect to the secondary interface 32 by making use of the information, in particular the address information and the credentials received from the server system 3 (action B5 in FIG. 3). Hence, a data connection in between the front-end computing device 2 and the server system 3 is established, wherein via the secondary interface 32 a data engine 33 of the server system 3 is enabled to communicate with the front-end computing device 2.

Following this concept, secondary interfaces 32 are dynamically created for specific requests, each secondary interface 32 being associated with a specific request and allowing a data communication only for that specific request.

Herein, multiple front-end computing devices 2 using multiple different applications can issue different requests to the server system 3, wherein for each request a dedicated secondary interface 32 for fulfilling only the associated, specific request is created.

Referring now to FIG. 4, infusion stations 1—being comprised of multiple pump devices 11 placed on a rack 10 or of a standalone pump device 12, as schematically indicated in FIG. 1—may communicate with the data engine 33 of the server system 3 via communication channels C1-C4, each communication channel C1-C4 for example using a dedicated protocol P1-P4 for transmitting and receiving data in an upstream direction A1 and in a downstream direction A2.

A first communication channel C1 herein may be a wireless channel, for example according to the Wi-Fi protocol and in addition using an HTTP protocol for the data transfer, for connecting an infusion station 1 having a pump device of a first type D1 and of a first family F1 to a front-end computing device 2. The same infusion station 1 herein may, alternatively or in addition, use a second communication channel C2, the second communication channel 2 for example being a wire-bound channel, such as an Ethernet channel adhering to the Ethernet protocol.

An infusion station 1 having a pump device of a different type D2, but of the same family F1, may use a third communication channel C3, for example also a wire-bound channel, but using a different protocol P3.

Another infusion station 1 having a pump device of type D1, but belonging to a different family F2, may use a communication channel C4, again using a different protocol P4 for communicating with a front-end computing device 2.

The pump type D1, D2 herein may indicate whether a pump device is a volumetric (peristaltic) infusion pump or a syringe infusion pump or another type of pump.

A device family F1, F2 may be defined by a certain manufacturer's brand, devices of the same family F1, F2 generally using a similar base architecture, for example a similar operating software.

Generally, dependent on what channel C1-C4 is used for transferring data, data messages m1-m3 are transferred according to the specifications of a specific protocol P1-P4, the protocol P1-P4 being used to pack the data messages m1-m3 according to the definitions of the protocol.

To enable a data communication between infusion stations 1 and a front-end computing devices 2 (once data connection via a dedicated secondary interfaces 32 are established), the data engine 33 of the server system 3 provides for a translation and abstraction in between infusion stations 1 and front-end computing devices 2. Both the infusion stations 1 and the front-end computing devices 2 shall communicate with the data engine 33, such that front-end computing devices 2 not necessarily must be enabled to communicate according to protocols P1-P4 being used by specific infusion stations 1 for specific communication channels C1-C4.

The data engine 33 implements driver modules DP1-DP4 which serve to provide for a communication with the infusion stations 1. In addition, virtual device modules VD1, VD2 are installed, the virtual device modules VD1, VD2 being configured to provide for a data communication with front-end computing devices 2.

The driver modules DP1-DP4 may for example be implemented by so-called dynamic-link libraries (.dll files), which e.g. within a Microsoft Windows operating system environment provide for dynamically linkable libraries of executable software code which may be employed by different software applications. Each communication channel C1-C4 using a specific protocol P1-P4 herein is associated with a specific driver module DP1-DP4, each driver module DP1-DP4 being enabled to provide for a communication using a specific protocol P1-P4.

Namely, in the example of FIG. 4, a first channel C1 using a first protocol P1, for example for a wireless data communication, exists associated with a first driver module DP1. A second communication channel C2, for example a wire-bound channel using a second protocol P2, such as an Ethernet channel according to the Ethernet protocol, is associated with a second driver module DP2. A third communication channel C3 using a third protocol P3 is associated with a third driver module DP3. A fourth communication channel C4 using a fourth protocol P4 is associated with a fourth driver module DP4.

Each driver module DP1-DP4 is configured to provide for a data communication via a specific, associated communication channel C1-C4 with an infusion station 1, the driver module DP1-DP4 managing the connection and being configured to process data for communication in the upstream direction A1 as well as in the downstream direction A2.

Namely, in the upstream direction A1 data which is being received via an associated communication channel C1-C4 is unpacked by removing a protocol framework used for transferring messages m1-m3. Such unpacked messages m1-m3 are then forwarded to an associated virtual device module VD1, VD2, as illustrated in FIG. 4. Within the virtual device modules VD1, VD2, as shall subsequently be explained in more detail, the data received from the driver modules DP1-DP4 is stored in a defined data model M (see FIG. 5), in which the data is organized in data structures M1, M10-M19.

In the downstream direction A2, in turn, each driver module DP1-DP4 is configured to process data messages m1-m3 received from an associated virtual device module VD1, VD2 to pack the data messages m1-m3 using the defined protocol framework of an associated protocol P1-P4, such that the data messages m1-m3 are forwarded to an infusion station 1 using that specific protocol P1-P4.

For communication in between the driver modules DP1-DP4 and the virtual device modules VD1, VD2 a common protocol, e.g., a protocol allowing for a queuing (buffering) of data messages, such as AMQP, may be employed.

Generally, data for transfer in the upstream direction A1 from infusion stations 1 towards the associated driver modules DP1-DP4 and virtual device modules VD1, VD2 may take place in a synchronous manner, the data transfer for example taking place in an event-triggered manner when data events occur, for example in the context of an infusion operation. The data engine 33 comprising the driver modules DP1-DP4 and the virtual device modules VD1, VD2 herein is configured to buffer and store data received from the infusion stations 1, such that stored data may be forwarded to front-end computing devices 2 when they are requested by a user U.

The virtual device modules VD1, VD2 serve to communicate with front-end computing devices 2. For each device family F1, F2, herein, one virtual device module VD1, VD2 may be implemented in the data engine 33 including a data model for the device family F1, F2. In the example of FIG. 4, a first device family F1 is associated with the virtual device module VD1. A second device family F2 is associated with the virtual device module VD2.

The virtual device modules VD1, VD2 in particular serve to store and consolidate information relating to infusion stations 1 and pump devices of such infusion stations 1.

In particular, within a virtual device module VD1, VD2 information relating to an identity of pumps of the associated device family F1, F2 may be stored, such information including information about the device family F1, F2, the pump type D1, D2, and a version of a pump device, such as a hardware version or an installed software version.

Alternatively or in addition, a virtual device module VD1, VD2 may store information relating to a pump status, such as a connectivity status, an infusion status, a location on a rack 10 of a pump device 11, a location of a pump device 11, 12 within a healthcare environment, such as a hospital, and the like. A connectivity status may include whether a pump device currently is connected to the communication network 4 or not, and—if yes—via which channel C1-C4. An infusion status may include whether an infusion operation is currently ongoing, and—if yes—which parameters are used for the infusion, such as a currently infused drug, a dose rate, an overall dosage, a time of infusion, and a time remaining for the infusion.

Alternatively or in addition, a virtual device module VD1, VD2 may store information relating to pump capabilities, wherein the capabilities may be different for different communication channels C1-C4 by means of which a specific infusion station 1 is connected to the communication network 4 and hence to the server system 3. For example, for a wireless communication channel C1 different capabilities may exist than for a wire-bound channel C2-C4. Such capabilities may relate to clinical functions and their availability, such clinical functions including for example an auto-programming function, an auto-documentation function, a drug library configuration function, a technical configuration function of a pump device, a firmware upload function, and a device event log function. For example, a firmware upload may only be possible if an infusion station is connected via a wire-bound communication channel C2-C4, but not via a wireless communication channel C1.

Referring now to FIG. 5, each virtual device module VD1, VD2 includes a data model M in which data relating to infusion stations 1 belonging to a device family F1, F2 associated with the virtual device module VD1, VD2 is stored in predefined, specific, dedicated data structures M1, M10-M19.

Herein, in the data model M for each infusion station 1 associated with a device family F1, F2 a data structure M1 exists including a tree of sub-structures. In the data structure M1 information relating to the particular infusion device is stored in dedicated structure elements.

In particular, in a first data structure M10 information relating to the virtual device module VD1, VD2 to which the infusion station 1 is associated may be stored.

In a second data structure M11 location information relating to the infusion station 1 may be stored, for example information identifying the exact physical location of the infusion station 1, such as information relating to a hospital, a ward, a room and a specific bed of a patient.

In a third data structure M12 information relating to the infusion station 1, such as information relating to a pump type, a pump family, a pump model and the like may be stored.

In a fourth data structure M13 information relating to a device status may be stored, relating for example to a status of an operating mode (for example "off", "standby", "booting", "on", "error", "maintenance"), a status of an infusion operation (for example "programming in progress", "installation in progress", "infusing", "stopped", "paused", "delayed infusion"), information relating to a battery status or the like may be stored.

In a fifth data structure M14 information relating to an alert may be stored, such as alarms and pre-alarms.

In a sixth data structure M15 information relating to a specific infusion may be stored. Herein, in a data sub-structure M16 information relating to a new prescription, and in a data sub-structure M17 information relating to a current prescription may be stored. In a substructure M18 relating to the data structure M17 herein global infusion information and current infusion information may be stored in data structures M18, M19. The data structure M18 relating to global infusion information herein may be associated with structure elements M180-M182 in which information relating to a patient (such as a patient's name, weight, height, gender and age), relating to a drug (such as a drug concentration and dilution) and relating to a care area (such as an intensive care unit) may be stored.

In the sub-structure M19 (associated with the data structure M17 identifying information relating to a current prescription) information relating to a current infusion operation may be stored, as is illustrated in an illustrative example in FIG. 6.

In particular, within the data structure M19 all information relating to a currently ongoing infusion operation may be stored, such as information relating to a programming mode (data structure M190, for example "time rate", "volume rate", "volume time", "volume time rate", "TCI", "ramp", "sequence"), information relating to a delivery mode (data structure M191, for example "standard", "manual bolus", "programmed bolus", "simple bolus", "priming"), information relating to a flow rate (data structure M192), information relating to a dose rate (data structure M193), information relating to a prescription volume (data structure M194), information relating to a remaining volume (data structure M195), information relating to an infused volume (data structure M196), information relating to an infused does (data structure M197), information relating to reasons why a delivery has failed (data structure M198), information relating to a dose completion status (data structure M199), information relating to a remaining duration of the infusion operation (data structure M200), information relating to a time until an end of a container from which medication is drawn in the context of a sequential infusion operation (data structure M201), and information relating to a remaining pause time (data structure M202).

Within the data model M, hence, defined pieces of information are stored in defined data structures. The information is extracted from communication messages received from infusion stations, the processing of the communication messages taking place by the driver modules DP1-DP4, which forwards the data to the virtual device modules VD1, VD2 for storing in the generic data model M. Front-end computing devices 2 may then exchange data with the data model M, such that information may be provided to the front-end computing devices 2, and vice versa information issued by the front-end computing devices 2 may be stored in the data model M and transferred on to relating infusion stations 1.

Referring now again to FIG. 4, a virtual device module VD1, VD2 uses a common protocol or a set of protocols for communication with a front-end computing device 2, wherein such protocol or set of protocols is unaffected by protocols P1-P4 used for communication with the infusion stations 1.

For the communication between the virtual device modules VD1, VD2 and the front-end computing devices 2, herein, different protocols may be used in the upstream direction A1 and in the downstream direction A2. In the upstream direction A1, for example, a queuing protocol, such as AMQP, may be used. In the downstream direction, in turn, an HTTP protocol, for example additionally employing XML and/or JSON, may be employed.

Generally herein, each virtual device module VD1, VD2 stores data d1-d5 extracted from messages m1-m3 received from infusion stations 1 (wherein each infusion station 1 may sent different messages containing different data) in for example a generic data model containing the pure data d1-d5. Such data is provided, upon a specific request, to a front-end computing device 2 according to a defined protocol VD (illustrated by a data transfer VD (d1, d2, d3, d4, d5) in FIG. 4) via a dedicated secondary interface 32 specifically created for that request.

Similarly as for the data transfer from the infusion stations 1 towards the virtual device modules VD1, VD2, a data transfer from the computing devices 2 towards the virtual device modules VD1, VD2 may take place in a synchronous, event-driven manner, for example in case a user U inputs information for example for programming an infusion station 1 and setting up an infusion operation. The virtual device modules VD1, VD2 store such information in the data model M, such that the information is transferred to one or multiple infusion stations 1 in a buffered manner for example once a communication becomes possible, for example once an infusion station 1 is connected to the communication network 4 by means of a specific communication channel C1-C4.

Referring now to FIG. 7, as described above the data engine 33 implements—in one embodiment—one or multiple virtual device modules VD1 and one or multiple driver modules D1, D2 for communicating with infusion stations 1 via different communication channels. Via the data engine 33, in particular via a virtual device VD1 implemented on the data engine 33, data is provided towards and received from a front-end computing device 2.

As illustrated in FIG. 7, the secondary interface 32 (data API) may comprise a logical processor 320 to which data is sent from the data engine 33 for transmission towards a front-end computing device 2 via a dedicated secondary interface 32. The logical processor 320 is responsible to process requests by one or multiple front-end computing devices 2 and to create data streams for communication with one or multiple front-end computing devices 2 using queuing and filtering techniques.

Referring now to FIGS. 8 and 9, data communication from a front-end computing device 2 in a downstream direction A2 (FIG. 8) and towards a front-end computing device 2 in an upstream direction A1 (FIG. 9) may take place differently.

In particular, as illustrated in FIG. 8, a communication in the downstream direction A2 may take place via a route R1 by accessing the server system 3 via the primary interface 30. The front-end computing device 2 hence transmits data, for example control data for an infusion device 1, such as drug library data, via the primary interface 30 and the administration engine 31 towards a virtual device VD1 associated with the particular infusion station 1. The virtual device 1 is hosted on the data engine 33, the data being stored within the data model M being included in the virtual device module VD1. Data may then be pushed in an asynchronous manner towards the infusion station 1 via a driver module D1, D2 and an associated communication path, the data for example being pushed towards the infusion station 1 dependent on their availability in the data model M of the virtual device module VD1.

In the upstream direction A1, in contrast, as illustrated in FIG. 9, data is transmitted towards a front-end computing device 2 using a route R2 via a dedicated secondary interface 32. In the upstream direction A1, hence, the data communication towards the front-end computing device 2 takes place via the secondary interface 32, which may for example be read-only such that a front-end computing device 2 may receive data from the secondary interface 32, but may not transmit data towards the secondary interface 32. For data transmission, the virtual device module VD1 forwards data towards the secondary interface 32, wherein the data is included in a corresponding data stream by means of the logical processor 320 according to the initial request of the front-end computing device 2 in the context of setting-up the data connection.

The virtual device VD1 may be enabled to manage data for data communication in between front-end computing devices 2 and infusion stations 1. In particular, a transmission of data in the downstream direction A2 or in the upstream direction A1 may depend on a specific communication channel, specific data transmissions being possible only via specific, dedicated communication channels.

For example, it may be the case that drug library data may be transmitted in the downstream direction A2 from a front-end computing device 2 towards an infusion station 1 only via a wireless communication channel by means of which an infusion station 1 is connected (directly or indirectly) to the server system 3. The virtual device module VD1 is enabled to detect whether a wireless communication channel with a particular infusion station 1 is available, and if this is the case it pushes drug library data towards the infusion station 1.

In another example, a monitoring involving data transmission of an infusion station 1 in the upstream direction A1 may be possible only via a wire-bound communication channel, such as an Ethernet connection in between an infusion station 1 and the server system 3. Again, the virtual device module VD1 is enabled to detect whether a wire bound connection to an infusion station 1 is available, and if this is the case a monitoring is enabled and data is transmitted towards a front-end computing device 2 to enable the monitoring.

The idea underlying the invention is not limited to the embodiments described above, but may be implemented in an entirely different fashion.

By means of a concept as described herein a data communication between front-end computing devices, in particular applications running on front-end computing devices, and a server system within a healthcare environment becomes possible in a logically organized fashion. Such communication may take place in an encrypted manner using a shared key which also is used for authentication when setting up a data connection.

A data communication herein may relate to data relating to infusion stations, such as pump devices arranged in a stack or standalone pumps. Such data may also relate to other information, for example patient-specific information, in a healthcare environment.

LIST OF REFERENCE NUMERALS

1 Infusion station
10 Rack
11 Medical device
12 Infusion station (medical device)

2 Front-end computing device
3 Server system
30 Primary interface
31 Administration engine
32 Secondary interface
320 Logical processor
33 Data engine
4 Communication network
5 Server device
A1 Upstream direction
A2 Downstream direction
B1-B5 Action
C1-C4 Communication channel
d1-d5 Extracted data
D1, D2 Device type
DP1-DP4 Driver module
F1, F2 Device family
m1-m3 Message
P1-P4 Protocol
R1, R2 Route
VD Virtual device protocol
VD1, VD2 Virtual device
U User

The invention claimed is:

1. A method for data communication between a server system and a front-end computing device in a healthcare environment, comprising:
transmitting, by the front-end computing device, a request for a data connection to a primary interface of the server system,
processing, by the server system, said request, and
establishing a data connection between the server system and the front-end computing device as a result of the processing,
said processing comprising dynamically creating a secondary interface on the server system dedicated to the request and transmitting information to access said secondary interface to the front-end computing device, and
said establishing comprising connecting, by the front-end-computing device, to said secondary interface using information received from the server system and transmitting data towards the front-end computing device via the secondary interface on the server system.

2. The method according to claim 1, wherein said processing includes verifying at least one of an authentication and an authorization based on the request according to information included in the request.

3. The method according to claim 2, wherein the authentication employs a pre-shared key.

4. The method according to claim 2, wherein the server system stores information about the authorization of an application of the front-end computing device to access data by means of the server system.

5. The method according to claim 1, wherein the information to access said secondary interface transmitted by the server system to the front-end computing device comprises at least one of a port number, credential information, and an IP address.

6. The method according to claim 1, wherein the server system comprises a data engine for transmitting data to or receiving data from the front-end computing device.

7. The method according to claim 6, wherein the data engine is in data connection with at least one infusion station.

8. The method according to claim 7, wherein the data engine communicates with the at least one infusion station using a driver module configured to receive, in an upstream direction, data from or transmit, in a downstream direction, data to the at least one infusion station.

9. The method according to claim 8, wherein the at least one infusion station uses a first communication protocol for communicating with the driver module.

10. The method according to claim 9, wherein the data engine communicates with the front-end computing device using a virtual device module configured to transmit, in the upstream direction, data to and receive, in the downstream direction, data from the front-end computing device,
wherein the driver module, in the upstream direction, processes data received from the at least one infusion station using said first communication protocol to provide said data to the virtual device module or, in the downstream direction, processes data received from the virtual device module to transmit said data to the at least one infusion station, and
wherein the virtual device module includes a data model defining a plurality of data structures in which data relating to the at least one infusion station is stored.

11. The method according to claim 10, wherein the virtual device module uses a second communication protocol for communicating with the front-end computing device.

12. The method according to claim 11, wherein the virtual device module, as the second communication protocol, uses an upstream protocol in the upstream direction and a downstream protocol different than the upstream protocol in the downstream direction.

13. The method according to claim 10, wherein the virtual device module stores data received from the at least one infusion station or from the front-end computing device in predefined data structures of the data model.

14. The method according to claim 10, wherein the virtual device module stores data relating to at least one of an identity of a pump device of an infusion station, a status of a pump device of an infusion station, and a capability of a pump device of an infusion station in predefined data structures of the data model.

15. A system for data communication in a healthcare environment, comprising:
a server system comprising a primary interface, and
a front-end computing device configured to transmit a request for a data connection to the primary interface of the server system, wherein the server system is configured to process said request in order to enable a data connection between the server system and the front-end computing device to be established as a result of the processing,
the server system being configured, during the processing, to dynamically create a secondary interface on the server system dedicated to the request and to transmit information to access said secondary interface to the front-end computing device, and
the front-end-computing device being configured to connect to said secondary interface using information received from the server system and to transmit data towards the front-end computing device via the secondary interface on the server system.

16. The method according to claim 1, wherein the secondary interface is an application programming interface.

17. The method according to claim 16, wherein the secondary interface comprises a logical processor.

18. The system according to claim 15, wherein the secondary interface is an application programming interface.

19. The system according to claim 18, wherein the secondary interface comprises a logical processor.

\* \* \* \* \*